United States Patent [19]
Ami

[11] Patent Number: 5,882,683
[45] Date of Patent: Mar. 16, 1999

[54] STICK COSMETICS AND PRODUCTION PROCESS FOR THE SAME

[75] Inventor: Kazuhiro Ami, Fujioka, Japan

[73] Assignee: Mitsubishi Pencil Kabushiki Kaisha, Tokyo, Japan

[21] Appl. No.: 580,735

[22] Filed: Dec. 29, 1995

[30] Foreign Application Priority Data

Jan. 9, 1995 [JP] Japan .............................. HEI 7-001441

[51] Int. Cl.⁶ .............................. A61K 7/02; A61K 7/48; A61K 7/021
[52] U.S. Cl. .............................. 424/489; 424/61; 424/63; 424/401
[58] Field of Search ................................ 424/61, 401, 63, 424/489

[56] References Cited

U.S. PATENT DOCUMENTS

| | | | |
|---|---|---|---|
| 3,800,034 | 3/1974 | Kircher et al. | 424/63 |
| 5,165,915 | 11/1992 | Tokubo et al. | 424/63 |
| 5,221,342 | 6/1993 | Minami et al. | 106/461 |

FOREIGN PATENT DOCUMENTS

| | | |
|---|---|---|
| 0 133 963 | 3/1985 | European Pat. Off. . |
| Sho 53-13491 | 3/1977 | Japan . |
| Sho 52-97399 | 8/1977 | Japan . |
| Sho 57-50741 | 10/1982 | Japan . |
| Sho 59-44305 | 3/1984 | Japan . |
| Sho 59-93014 | 5/1984 | Japan . |
| Sho 61-197507 | 1/1986 | Japan . |
| Sho 61-176513 | 8/1986 | Japan . |
| Sho 61-176513 | 8/1986 | Japan . |
| Sho 61-225107 | 10/1986 | Japan . |

OTHER PUBLICATIONS

Chemical Abstracts, Jan. 23, 1978, Synthetic High Polymers.

*Primary Examiner*—Thurman K. Page
*Assistant Examiner*—Sharon Howard
*Attorney, Agent, or Firm*—Darby & Darby

[57] ABSTRACT

The present invention provides a stick cosmetic which is not oily when it is applied to skin and is not softened at high temperatures and which is adhered to the skin with a powdery and smooth feeling when it is applied to the skin while having a sufficiently large flexural strength and is suitable for eyebrows and eyeliner having a sufficiently good color tone. That is, the present invention relates to a stick cosmetic which has a porosity of 5 to 45% and in which the pores are impregnated with silicone oil, oil & fat or wax, comprising 1 to 10 weight % of at least one clay selected from the group consisting of bentonite, smectite, montmorillonite, bederite, nontronite, hectorite, and saponite, an inorganic extender pigment, and an inorganic color pigment as essential components, wherein the above inorganic fine particles leaving no carbides in sintering at 300° to 1000° C. are kneaded with water; the kneaded composition is molded; this molded composition is dried and then subjected to heat treatment at 300° to 1000° C., and a production method of the same.

11 Claims, No Drawings

STICK COSMETICS AND PRODUCTION PROCESS FOR THE SAME

BACKGROUND OF THE INVENTION (1) Field of the Invention

The present invention relates to solid stick cosmetics such as eyebrow and eyeliner, which are powdery (easy to become powdery) and which are excellent in usability and have a sufficiently good color tone, and a production process for the same.

(2) Description of Prior Art

Conventional solid stick cosmetics are obtained by kneading a colorant and a filler with waxes such as oil & fat, wax, fatty acid, and hydrocarbon as a binder and molding the mixture to a stick. Since they are oily when they are applied to skin, and the waxes are softened in a place of high temperatures, not only physical odd is felt upon the application thereof to skin, but also it is difficult to maintain the shape of the stick cosmetics. Further, since the stick cosmetics are very liable to be broken in using them if the amounts of waxes are increased in order to obtain a sufficiently large breaking strength, it results hardening the stick cosmetics and causing them to lack in adhesion to skin and smoothness.

Thus, since the solid stick cosmetics using waxes for a binder have oiliness peculiar to the waxes, a powdery (a dry and smooth feeling like powder) use feeling can not be obtained, and it has been difficult to satisfy a sufficiently large breaking strength and a good application feeling to skin at the same time.

Accordingly, stick cosmetics which are intended to obtain a powdery use feeling without using waxes are investigated. Proposed are those using water soluble adhesive pastes such as CMC (carboxymethyl cellulose) for a binder (Japanese Patent Application Laid-Open No. Sho 59-44305) and those using gypsum for a binder (Japanese Patent Application Laid-Open No. Sho 59-93014).

However, since the binders are extremely hardened in the stick cosmetics using these binders, an application feeling to skin is very stiff. Further, applying these binders to thin articles such as eyebrow and eyeliner makes them very breakable, and increasing the amount of the binder in order to obtain a sufficiently large breaking strength makes it impossible at all to apply them to skin.

That is, it is difficult, for stick cosmetics in which water soluble adhesive pastes such as CMC or gypsum are substituted for waxes as a binder in order to obtain a powdery use feeling, to satisfy a sufficiently large breaking strength and a good application feeling at the same time. Further, stick cosmetics which satisfy a sufficiently large breaking strength and a good application feeling at the same time without using waxes are investigated as well, and proposed are those in which clay is used for a binder and the clay is sintered (Japanese Patent Application Laid-Open No. Sho 61-176513) and those in which a pore-forming material is used to prepare a more porous sintered substance (Japanese Patent Application Laid-Open No. Sho 61-197507). The invention disclosed in Japanese Patent Application Laid-Open No. Sho 61-176513 provides the stick cosmetics in which an inorganic pigment dispersed in a powder form is incorporated into a sintered substance of clay having a porous skeleton formed by providing sintering treatment. According to the descriptions of the above publication, the term "porous" means "the larger the porosity is, the better the touch and applicability in use tend to become, and the smaller and more minute the porosity is, the more the strength tend to increase". In the end, disclosed by the above publication is a sintered substance having a porosity of a level of 50 to 90%.

That is, while a sintered substance of clay provides a sufficiently large breaking strength, it is hard and therefore difficult to be applied to skin. However, turning it to a porous sintered substance provides a stick cosmetic which satisfy a sufficiently large breaking strength and a good application feeling at the same time.

The invention disclosed in the claims of Japanese Patent Application Laid-Open No. Sho 61-176513 described above can not provide a desired color tone and quality the stick cosmetics have to provide.

The control of a porosity is indispensable in order to satisfy a good application feeling and a sufficiently large breaking strength at the same time, but it is very difficult to obtain a sintered substance having such a preferred porosity of a level of 50 to 90% as described in the above publication only by changing temperatures in sintering treatment and a use proportion of clay and a powdered pigment as described in the above publication. In order to obtain the porosity falling in such the range, needed are means by which an excipient and a molding aid of various resins added for molding are removed by burning them in an oxidation atmosphere in sintering treatment, or pores are formed by removing them by depolymerization in an inert atmosphere, as described in the examples of the above publication, or means by which pores are intentionally formed by using the pore-forming agent disclosed in Japanese Patent Application Laid-Open No. Sho 61-197507.

However, in the method for removing various resins added for molding by burning them in an oxidation atmosphere in sintering treatment, colored pigments are oxidized as well in the sintering treatment, and therefore when colored pigments which are susceptible to oxidation, such as black pigments including black iron oxide, carbon black and titan black are used, they are discolored or faded. Accordingly, a desired color tone can not be developed.

In the method for removing various resins by depolymerization in an inert atmosphere, the resins are practically turned into carbides and remains in stick cosmetics. Accordingly, it is very difficult to remove them completely. As a result thereof, the stick cosmetics become blackish, and therefore a desired color tone can not be developed. Further, even when resins which leave relatively less carbides, such as polymethyl methacrylate are used, the carbides remain, though only slightly, in the stick cosmetics, and a method for burning the resins in an oxidation atmosphere has to be resulting employed in order to remove them completely. Furthermore, these carbides not only prevent a desired color tone from being developed but also form variant primary substances as well. Further, in depolymerizing polymethyl methacrylate, the resulting monomers have a high toxicity, which causes a serious problem on the safety of cosmetics.

In a method in which pores are formed by using a pore-forming agent and removing it by chemical treatment after sintering treatment as disclosed in Japanese Patent Application Laid-Open No. Sho 61-197507, there is no concern about remaining carbides as described above. However, it is very difficult to remove the pore-forming agent from stick cosmetics by the chemical treatment. As a matter of fact, when removing the pore-forming agent by such the method, a method in which the pore-forming agent is eluted from stick cosmetics by chemicals is used. Accordingly, the forms of the stick cosmetics are broken, and it is almost impossible to remove completely the pore-forming agent while maintaining the forms thereof.

Since the pore-forming agent results in remaining in the stick cosmetics as an impurity, not only sufficient pores are not formed but also a problem on quality is presented in terms of safety as cosmetics.

The methods described in Japanese Patent Application Laid-Open No. Sho 52-97399, Japanese Patent Publication No. Sho 53-13491 and Japanese Patent Publication No. Sho 57-50741 are proposed as a method for obtaining the sintered substance of an inorganic pigment having a sufficiently good color tone. However, all of these methods apply to pigments or fine particles and do not apply to stick cosmetics. In other words, while fine particles used for cosmetics having a sufficiently good color tone can be obtained when these methods are used, it is impossible to mold fine particles to sticks and maintain the form thereof, and therefore solid stick cosmetics can not be obtained at all.

The method described in Japanese Patent Application Laid-Open No. Sho 61-225107 is proposed as a method for obtaining solid stick cosmetics having various color tones.

However, this method causes a color change by heat treatment, and therefore when two or more kinds of colorants are contained at the same time, the respective colorants cause independently characteristic color changes, for example, if a brown color is intended to develop with black iron oxide and red iron oxide, the heat treatment discolors independently black iron oxide and red iron oxide, and the desired brown color can not be developed. In short, the method in which colors are changed by heat treatment limits the resulting color tones and makes it very difficult to obtain various color tones necessary for stick cosmetics.

SUMMARY OF THE INVENTION

An object of the present invention is to provide a solid cosmetic in which a sufficiently large strength, a powdery application feeling to skin and a desired color tone are obtained at the same time by using clay of such a small amount as 1 to 10 weight % such as bentonite, kneading an inorganic extender pigment such as kaolin leaving no carbide at all in sintering and an inorganic color pigment with water and sintering the mixture.

The present invention relates to a stick cosmetic prepared by kneading a composition comprising an inorganic powder which contains 1 to 10 weight % of at least one clay selected from the group consisting of bentonite, smectite, montmorillonite, bederite, nontronite, hectorite, and saponite, an inorganic extender pigment, and an inorganic color pigment as essential components and which leaves no carbides in sintering at 300° to 1000° C., and water, molding the kneaded composition to a stick, drying the resulting molded composition, and subjecting it to heat treatment at temperatures falling within a range of 300° to 1000° C., and a production method for the same.

Kaolin is most preferred as the inorganic extender pigment, and in addition thereto, used is at least one selected from the group consisting of calcium carbonate, mica, boron nitride, spherical silica, and talc.

Used as the inorganic color pigment is at least one selected from the group consisting of titanium oxide, black iron oxide, carbon black, chromium oxide, ultramarine, and red iron oxide.

Sintering by heat treatment is carried out in an inert environment at temperatures falling within a range of 300° to 1000° C., preferably 400° to 800° C., and more preferably 500° to 700° C.

Pores formed by heat treatment sintering resids in a proportion of 5 to 45%, preferably 15 to 30%.

The pores formed by the heat treatment sintering are preferably impregnated with at least one oil & fat or wax selected from the group consisting of silicone oil, natural oil & fat, and hydrocarbons.

DETAILED DESCRIPTION OF THE PREFERRED EMBODIMENTS

Intensive investigations made by the present inventors in order to solve the problems described above have resulted in finding that they can be solved by using no waxes as a binder, using a small amount of specific clay such as bentonite as a binder, using an inorganic extender pigment and an inorganic color pigment each leaving no carbide at all in sintering, and impregnating the pores formed in sintering with silicone oil, oil & fat or the like, and completing the present invention.

In the present invention, 1 to 10 weight % of at least one clay selected from the group consisting of bentonite, smectite, montmorillonite, bederite, nontronite, hectorite, and saponite, an inorganic extender pigment, and an inorganic color pigment are blended as essential components. All of these inorganic powders are inorganic powders which do not leave carbides at all in a sintering process at temperatures falling within a range of 300° to 1000°.

These inorganic powders are mixed, and water is added to knead the composition. Then, the kneaded composition is molded to a stick and dried. This dried stick is subjected to heat treatment in an inert atmosphere at temperatures falling within a range of 300° to 1000° C., preferably 400° to 800° C., and more preferably 500° to 700° C., and sintered. In this case, the porosity can be 5 to 45%, preferably 15 to 30%.

The pores formed in this sintered stick may be impregnated with at least one oil & fat or wax selected from the group consisting of silicon oil, natural oil & fat, and hydrocarbon, which is rather preferred in terms of an application feeling to skin.

In the present invention, 1 to 10 weight % of at least one clay selected from the group consisting of bentonite, smectite, montmorillonite, bederite, nontronite, hectorite, and saponite is used as the clay.

As a matter of course, they do not leave carbides at all by sintering at 300° to 1000° C.

Kaolin, calcium carbonate, mica, boron nitride, spherical silica, and talc can be given as the inorganic extender pigment. As a matter of course, they also do not leave carbides at all by sintering at 300° to 1000° C.

Titanium oxide, black iron oxide, carbon black, chromium oxide, ultramarine, and red iron oxide can be given as the inorganic color pigment. They also neither cause color change nor generate carbides by sintering at 300° to 1000° C. if the sintering is carried out in an inert atmosphere. The sintering is carried out preferably at 700° C. or lower in a sense to prevent a change in the color of the pigment.

The sintering temperature falls within a range of 300° to 1000° C., preferably 400° to 800° C., and more preferably 500° to 700° C.

In the stick cosmetic of the present invention, pores of 5 to 45% are formed after molding and sintering. The pores of less than 5% harden the stick cosmetic and the powdery and good application feeling can not be obtained. The pores of more than 45% lower the flexural strength, on account of the content of clay being 1 to 10 weight %. The porosity falls preferably in a range of 15 to 30%.

In the stick cosmetic of the present invention, waxes are not used at all as a binder, and the pores can be impregnated with oil & fat and waxes such as silicone oil, various oil % fats, and hydrocarbons, which is rather preferred in terms of an application feeling to skin.

The stick cosmetic of the present invention does not use at all waxes as a binder, which are oily in applying to skin and softened at elevated temperatures. While specific clay is used in such a small amount as 1 to 10 weight %, and this tends to reduce the flexural strength, resins which are removed by oxidation or depolymerized in sintering are not used at all, that is, binders which are usually used for increasing the porosity to 50 to 90% and leave carbides after sintering are not used at all, and instead, the porosity is reduced to 5 to 45% to secure the flexural strength, whereby a change in a color tone is prevented, and the stick cosmetic having a large safety and a powdery and good application feeling is obtained.

As described above, the pores formed after sintering can be impregnated with a small amount of oil & fat or wax in order to improve an application feeling.

EXAMPLES

The present invention will more concretely be explained below with reference to examples, but the present invention will not be restricted by these examples.

In the examples, the term "parts" means weight parts.

Example 1

| Bentonite | 8 parts |
| --- | --- |
| Kaolin | 50 parts |
| Boron nitride | 12 parts |
| Titanium oxide | 30 parts |

The blend materials described above were evenly mixed with a mixer, and purified water 20 parts was added. After kneading the above materials with a rolling mill, the kneaded composition was molded to a stick having a diameter of 2.2 mm with an extrusion molding machine, and the stick was dried at 150° C. for 2 hours to remove water completely. The dried stick was put on a vessel made of ceramics, and an atmosphere in the vessel was completely replaced with nitrogen gas. This was maintained at 650° C. for one hour in an inert atmosphere in an electric furnace to subject it to heat treatment.

After cooling down, the white stick providing a powdery and good application feeling when the stick was applied to skin was obtained.

The stick was dipped in a silicone oil and taken out after leaving for standing for one hour to remove surplus silicone oil with a centrifugal separator.

This was cut to a length of 40 mm. The stick had a porosity of 25% before impregnated with silicone oil. Remark: the porosity was measured by a substitution method (20° C.). That is, the porosity is expressed by the following equation:

$$\text{porosity} = 100 \times (W'-W)/\rho V (\%)$$

wherein V is the volume of the stick: W is the weight thereof; W' is the weight of the stick after impregnated with water; and $\rho$ is the density of water.

Example 2

| Saponite | 4 parts |
| --- | --- |
| Kaolin | 26 parts |
| Calcium carbonate | 25 parts |
| Mica | 25 parts |
| Black iron oxide | 10 parts |
| Titanium oxide | 10 parts |
| Purified water | 50 parts |

The blend materials described above were used. A dark grey stick having a porosity of 20% was obtained in the same manner as that in Example 1.

Example 3

| Saponite | 5 parts |
| --- | --- |
| Kaolin | 45 parts |
| Boron nitride | 20 parts |
| Carbon black | 10 parts |
| Red iron oxide | 20 parts |
| Purified water | 40 parts |

The blend materials described above were used. A brown stick having a porosity of 18% was obtained in the same manner as that in Example 1.

Example 4

| Montmorillonite | 2 parts |
| --- | --- |
| Kaolin | 47 parts |
| Spherical silica | 20 parts |
| Chromium oxide | 10 parts |
| Titanium oxide | 20 parts |
| Purified water | 40 parts |

The blend materials described above were used. A light green stick having a porosity of 22% was obtained in the same manner as that in Example 1.

Example 5

| Bentonite | 6 parts |
| --- | --- |
| Kaolin | 54 parts |
| Talc | 20 parts |
| Ultramarine | 20 parts |
| Purified water | 40 parts |

The blend materials described above were used. A blue stick having a porosity of 23% was obtained in the same manner as that in Example 1.

Comparative Example 1—example of conventional core comprising primarily wax

| Bees wax | 20 parts |
| --- | --- |
| Ozokelite | 10 parts |
| Microcrystalline wax | 10 parts |
| Carnauba wax | 8 parts |
| Vaseline | 7 parts |
| Lanolin | 5 parts |
| Liquid paraffin | 7 parts |
| Isopropyl myristate | 4 parts |

The blend materials described above were dissolved, and black iron oxide of 10 parts and red iron oxide of 19 parts were added thereto. After stirring and dispersing, the mixture was kneaded with a mixer and cooled down to room temperatures. Then, the kneaded mixture was molded to a brown stick having a diameter of 2.2 mm with an extrusion molding machine, and the stick was cut to a length of 40 mm, whereby a stick was obtained.

Comparative Example 2—example of a stick used more than 10 weight % by Bentonite,

| Bentonite | 20 parts |
| Kaolin | 50 parts |
| Carbon black | 10 parts |
| Red iron oxide | 20 parts |

The blend materials described above were used. A brown stick in the same manner as that in Example 1.

Comparative Example 3—example using polymethyl methacrylate of Japanese Patent Application No. Sho 61-176513

| Bentonite | 20 parts |
| Titanium oxide | 60 parts |
| Polymethyl methacrylate | 30 parts |
| Dioctyl phthalate | 30 parts |
| Methyl ethyl ketone | 100 parts |

After kneading the blend materials described above with a mixer and a mill, the kneaded composition was heated at 250° C. to remove sufficiently methyl ethyl ketone and dioctyl phthalate, and then this was molded to a stick having a diameter of 2.2 mm with an extrusion molding machine while heating at 230° C. The temperature was raised gradually up to 300° C., and then the stick was maintained at a maximum temperature of 800° C. for one hour in a non-oxidizing atmosphere in an electric furnace to subject it to heat treatment.

The article obtained after cooling down was a light gray stick.

This stick was dipped in silicone oil and taken out after leaving for standing for one hour to remove surplus silicone oil with a centrifugal separator.

This was cut to a length of 40 mm.

Comparative Example 4—example using a pore-forming material of Japanese Patent Application Laid-Open No. 61-197507

| Bentonite | 20 parts |
| Red iron oxide | 20 parts |
| Black iron oxide | 10 parts |
| Carbon black | 30 parts |
| Polymethyl methacrylate | 30 parts |
| Dioctyl phthalate | 30 parts |
| Methyl ethyl ketone | 100 parts |

The blend materials described above were used to obtain a brown stick in the same manner as that in Comparative Example 3, except that the heat treatment of up to 800° C. was carried out in an oxidizing atmosphere in place of a non-oxidizing atmosphere.

The sticks obtained in Examples 1 to 5 and Comparative Examples 1 to 4 were evaluated for a flexural strength, an application feeling to skin, and a color change by the following evaluating methods.

Flexural Strength:

A load was applied to the central part of a stick having a diameter d (mm) supported on two fulcrums (distance between the fulcrums: 22 mm) at a rate of 10 mm per minute at 30° C., and the flexural strength was calculated from the load P (gf) by which the stick was broken according to the following equation, wherein the forms of an end by which the load is applied and the ends of both the fulcrums are semicircles having a radius (R) of about 0.2 mm:

Flexural strength=$8 \times P \times 22/\pi d^3 (gf/mm^2)$

Application Feeling to Skin:

With respect to the application feeling obtained when stick cosmetics were applied to skin, a sensuous evaluation of four grades was carried out by 20 female panelers according to the following criteria, and the values obtained were averaged:

⊚:good, ○:slightly good, ▲:too hard, and ▼:too soft.

Chance in Color Tones:

With respect to the change in color tones caused by heat treatment, a sensuous evaluation of three grades regarding to a change in the respective color tones was carried out, wherein the stick cosmetics before and after the heat treatment were applied to skin:

○:no change observed, Δ:change in color tone observed, and x:color tone changed completely.

TABLE 1

| | Flexural strength (gf/mm$^2$) | Application feeling to skin | Change in color tone |
|---|---|---|---|
| Example 1 | 760 | ○ | ○ |
| Example 2 | 430 | ⊚ | ○ |
| Example 3 | 560 | ⊚ | ○ |
| Example 4 | 400 | ⊚ | ○ |
| Example 5 | 520 | ⊚ | ○ |
| Comp. Example 1 | 150 | ▼ | ○ |
| Comp. Example 2 | 1080 | ▲ | ○ |
| Comp. Example 3 | 460 | ○ | Δ |
| Comp. Example 4 | 410 | ○ | x |

As can be found from the results shown in Table 1, while all of the sticks obtained in the examples are good in terms of the application feeling to skin and the change in a color tone, the flexural strength is half or less in Comparative Example 1 as compared with those of the examples, and the application feeling to skin is too soft.

The stick obtained in Comparative Example 2 is too hard and therefore has not been able to be applied to skin.

In Comparative Example 3, carbide remains, and therefore the color tone has been darkened.

In Comparative Example 4, the colorant has been oxidized, and therefore the color tone has been completely changed.

Thus, The stick cosmetics according to the present invention have the excellent form-maintaining characteristic and can express the sufficiently good color tones. They have a powdery use feeling and are the good solid stick cosmetics.

Binders leaving carbides in sintering are not used at all in the present invention, and clay such as bentonite is used in such a small amount as 1 to 10 weight %. Accordingly, the porosity has been reduced to 5 to 45%, whereby the solid stick cosmetics which have achieved sufficiently large strengths, powdery application feelings to skin, and desired color tones at the same time have been able to be obtained.

What is claimed is:

1. A stick cosmetic with a porosity of from 5 to 45%, prepared by kneading a composition comprising an inorganic powder which contains 1 to 10 weight % of at least one clay selected from the group consisting of bentonite, smectite, montmorillonite, bederite, nontronite, hectorite, and saponite, an inorganic extender pigment, and an inorganic color pigment as essential components and which leaves no carbides in sintering at 300° to 1000° C., and water, molding the kneaded composition to a stick, drying the resulting molded composition, and subjecting it to heat treatment at temperatures falling within a range of 300° to 1000° C.

2. A stick cosmetic as described in claim 1, wherein the inorganic extender pigment is at least one selected from the group consisting of kaolin, calcium carbonate, mica, boron nitride, spherical silica, and talc.

3. A stick cosmetic as described in claim 1, wherein the inorganic extender pigment is kaolin.

4. A stick cosmetic as described in claim 1, wherein the inorganic color pigment is at least one selected from the group consisting of titanium oxide, black iron oxide, carbon black, chromium oxide, ultramarine, and red iron oxide.

5. A stick cosmetic as described in claim 1, wherein pores formed by heat treatment sintering are impregnated with at least one oil and fat or wax selected from the group consisting of silicone oil, natural oil and fat, and hydrocarbons.

6. A method for producing a stick cosmetic comprising:
   mixing evenly an inorganic powder containing 1 to 10 weight % of at least one clay selected from the group consisting of bentonite, smectite, montmorillonite, bederite, nontronite, hectorite, and saponite, an inorganic extender pigment, and an inorganic color pigment as essential components and leaving no carbides in sintering at temperatures of 300° to 1000° C.,
   adding purified water to the inorganic powder and kneading it,
   then molding a kneaded composition to a stick with an extrusion molding machine,
   drying the stick to remove water completely, and
   subjecting the dried stick in an inert gas atmosphere to heat treatment at temperatures falling within a range of 300° to 1000° C. to sinter it.

7. A method for producing a stick cosmetic as described in claim 6, wherein the stick cosmetic having pores formed by the heat treatment sintering is dipped in at least one selected from the group consisting of silicone oil, liquid oil & fats, and molten waxes and taken out after leaving for standing for a fixed time to remove surplus oil with a centrifugal separator.

8. A method for producing a stick cosmetic as described in claim 6, wherein the inorganic extender pigment is at least one selected from the group consisting of kaolin, calcium carbonate, mica, boron nitride, spherical silica, and talc.

9. A method for producing a stick cosmetic as described in claim 6, wherein the inorganic color pigment is at least one selected from the group consisting of titanium oxide, black iron oxide, carbon black, chromium oxide, ultramarine, and red iron oxide.

10. A method for producing a stick cosmetic as described in claim 6, wherein the heat treatment sintering is carried out at temperatures falling in a range of 500° to 700° C.

11. A method for producing a stick cosmetic as described in claim 6, wherein the porosity by the heat treatment sintering is 15 to 30%.

* * * * *